(12) United States Patent
Loozens

(10) Patent No.: US 7,655,653 B2
(45) Date of Patent: Feb. 2, 2010

(54) TETRAHYDROBENZFLUORENE DERIVATIVES

(75) Inventor: Hubert Jan Jozef Loozens, Oss (NL)

(73) Assignee: N.V. Organon, Oss (NL)

( * ) Notice: Subject to any disclaimer, the term of this patent is extended or adjusted under 35 U.S.C. 154(b) by 130 days.

(21) Appl. No.: 11/924,507

(22) Filed: Oct. 25, 2007

(65) Prior Publication Data

US 2008/0058361 A1 Mar. 6, 2008

Related U.S. Application Data

(63) Continuation of application No. 10/499,956, filed as application No. PCT/EP02/14283 on Dec. 16, 2002, now Pat. No. 7,304,155.

(30) Foreign Application Priority Data

Dec. 21, 2001 (EP) .................. 01205206

(51) Int. Cl.
*A61K 31/5375* (2006.01)
*A61K 31/495* (2006.01)
*C07D 265/30* (2006.01)
*C07D 241/04* (2006.01)

(52) U.S. Cl. ............... 514/238.8; 544/106; 544/154; 544/358; 546/184; 546/248; 548/528; 514/231.2; 514/252.12; 514/315

(58) Field of Classification Search ............... 544/106, 544/154, 358; 546/184, 248; 548/528; 514/231.2, 514/238.8, 252.12, 315

See application file for complete search history.

(56) References Cited

U.S. PATENT DOCUMENTS 5,147,880 A 9/1992 Jones .................. 514/319
7,304,155 B2 * 12/2007 Loozen .................. 544/106

FOREIGN PATENT DOCUMENTS

| EP | 0 524 742 A | 1/1993 |
|---|---|---|
| EP | 0524742 A | 1/1993 |
| WO | WO 01/72713 A1 | 10/2001 |
| WO | WO 01/72713 A1 | 10/2001 |

OTHER PUBLICATIONS

Tedesco, R. et al. "Synthesis and Evaluation of hexahydrochrysene and tetrahydrobenzofluorence Ligands for the Estrogen Receptor," *Bioorg Med Chem Lett* 11 (2001) 1281-1284, XP001503388 cited in the application p. 1282.

Tedesco, R. et al, "Snythesis and Evaluation of hexahydrochrysene and Tetrahydrobenzofluorence Ligands for the Estrogen Receptor" Bioorganic & Medicinal Chemistry Letters (2001), 11(10), 1281-1284, May 21, 2001 XP001053388 cited in the application p. 1282.

* cited by examiner

*Primary Examiner*—Golam M Shameem
(74) *Attorney, Agent, or Firm*—Susan Hess

(57) ABSTRACT

A compound having the formula I

Formula I wherein
the O—$(CH_2)_n$—$N(R^1,R^2)$ substituent on the phenyl ring can be in meta or para position;
n is 2-4
$R^e$ and $'R^e$ are OH, optionally independently etherified or esterified;
$R^1$ and $R^2$ are independently (1C-4C)alkyl, (2C-4C)alkenyl, hydroxy(2C-4C)alkyl, (1C-3C)alkoxy(2C-4C)alkyl, aryl or aryl(1C-2C)alkyl; or $R^1$ and $R^2$ together with the nitrogen form an aromatic or non-aromatic heterocyclic ring structure, optionally mono- or poly-substituted with (1C-4C)alkyl, (2C-4C)alkenyl, hydroxy(1C-2C)alkyl, (1C-2C)alkoxy(1C-3C)alkyl or aryl. These compounds can be used for estrogen receptor β selective medical treatments.

5 Claims, No Drawings

TETRAHYDROBENZFLUORENE DERIVATIVES

RELATED APPLICATION

This application is a continuation of U.S. application Ser. No. 10/499,956 filed Jan. 25, 2005, now U.S. Pat. No. 7,304,155 which claims priority based on International Patent Application No. PCT/EP2002/14283 filed on Dec. 16, 2002, and European Patent Application No. 01205206.4, filed Dec. 21, 2001.

FIELD OF THE INVENTION

The invention relates to tetrahydrobenzfluorene derivatives and to compounds having anti-estrogenic activity.

BACKGROUND OF THE INVENTION

Compounds with affinity for estrogen receptors have found long-standing utility in the treatment of a variety of medical indications. Despite the long history of the field there still is a need for more effective, safer and more economical compounds than the existing ones. For the control or prevention of estrogen sensitive tumor growth, compounds are needed which are antagonists or partial antagonists.

The discovery of subtypes of estrogen receptors, there being an α-subtype (ERα) and a β-subtype (ERβ) of such receptors (Mosselman et al., *FEBS Letters* vol. 392 (1996) pp. 49-53 as well as EP-A-0 798 378), offers the possibility to influence one particular subtype of those two receptors more selectively, immanently resulting in more effective treatments or treatments with less side effects. Since these receptors have a different distribution in human tissue, the finding of compounds which possess a selective affinity for either of the two is an important technical progress, making it possible to provide a more selective treatment in estrogen-receptor related medical treatments with a lower burden of estrogen-related side-effects.

Attempts to replace the steroid skeleton with other cyclic structures have led to explorations of a tetrahydrobenzfluorene skeleton (Tedesco et al.; Bioorganic Med Chem Letters Vol 11, pp 1281-1284; 2001) as compounds with influence on estrogen receptors. Compounds with a differing tetrahydrobenzfluorene skeleton were found, which within strict stereochemical requirements, display very selective actions on estrogen receptors.

It is found that compounds having the formula I

Formula I wherein
the O—(CH$_2$)$_n$—N(R$^1$,R$^2$) substituent on the phenyl ring can be in meta or para position;
n is 2-4
R$^e$ and 'R$^e$ are OH, optionally independently etherified or esterified;

R$^1$ and R$^2$ are independently (1C-4C)alkyl, (2C-4C)alkenyl, hydroxy(2C-4C)alkyl, (1C-3C)alkoxy(2C-4C)alkyl, aryl or aryl(1C-2C)alkyl; or R$^1$ and R$^2$ together with the nitrogen form an aromatic or non-aromatic heterocyclic ring structure, optionally mono- or poly-substituted with (1C-4C)alkyl, (2C-4C)alkenyl, hydroxy(1C-2C)alkyl, (1C-2C)alkoxy(1 C-3C)alkyl or aryl.

The compounds of the invention can be used in medical treatments aimed to selectively influence estrogen receptors (ERα, and ERβ) in an organism, being a human or an animal.

DETAILED DESCRIPTION OF THE INVENTION

An embodiment of the invention is the group of compounds wherein:
the O—(CH$_2$)$_n$—N(R$^1$,R$^2$) substituent on the phenyl ring is in the meta position;
n is 2 or 3
R$^e$ and 'R$^e$ are OH
R$^1$ and R$^2$ independently are benzyl, (1C-4C)alkyl, hydroxy(2C-4C)alkyl, (1C-3C)alkoxy(2C-4C)alkyl or together with the nitrogen form a non-aromatic ring selected from the list morpholino, piperidino, pyrrolidino, tetrahydropyridyl and piperazinyl, whereby the morpholino, piperidino, pyrrolidino, tetrahydropyridyl can be optionally substituted with (1C-2C)alkyl and the piperazinyl can be optionally substituted at distal nitrogen (4) with (1C-4C)alkyl, (2C-4C)alkenyl, (1C-2C)alkoxy(1C-2C)alkyl or aryl.

A specific embodiment of the invention is the compound having formula II

Formula II

The terms used in the definitions above have the limited meaning as follows:
Alkyl is a branched or unbranched alkyl group, for example methyl, ethyl, propyl, isopropyl, butyl, sec-butyl, tert-butyl;
Alkenyl is a branched or unbranched alkenyl group, such as ethenyl, 2-butenyl, etc.;
Aryl is an aromatic carbon, and optionally nitrogen, containing ring structure such as phenyl, pyrimidinyl, pyridyl, imidazolyl.

The prefixes (1C-4C), (2C-4C) etc. have the usual meaning to restrict the meaning of the indicated group to those with 1 to 4, 2 to 4 etc. carbon atoms.

Compounds of the invention can be synthesized according to the route described in Scheme I. The starting ketone 1, possessing the cis stereochemistry underwent stereoselective addition of protected phenolic Grignard reagents, providing the alcohols 2, 3. Subsequent mild dehydration (e.g. with aqueous or alcoholic solutions of acids like HCl, or H$_2$SO$_4$, or trifluoroacetic acid or with reagents like SOCl$_2$ in pyridine) provides the dihydrosystem 4. Dissolving metal reduction (in this case lithium in liquid ammonia), provides predominantly the required cis-anti stereochemistry, referring to the tertiary hydrogens as indicated in the scheme. Some minor isomer impurities (cis-syn) can be removed easily by chromatography of 6. Attachment of the basic side chain to the phenolic moiety (steps 6→11) is performed by means of routine procedures, many of which belong to textbook chemistry. As the desired products 11, 12 contain chiral centers, they consist of two antipodes. In order to make available the R- and S-enantiomers of 11 and 12 in principle a number of chiroptical techniques may be used such as resolution by means of chiral column chromatography (coated cellulose columns and the like) classical resolution of diastereomeric salts or of separable chiral derivatives (diastereoisomeric esters and the like) of the intermediates or by means of enantioselective synthesis.

We found that synthesis of the optical antipodes of the products claimed is easily achieved by starting from the enantiomers of ketone 1. These can be synthesized by making use of the procedure described in Scheme II. Enzymatic resolution of the racemic cis hydroxymethyl derivative (+/−13), using porcine pancreatic lipase and vinyl acetate provided a 1:1 mixture of the (+)-alcohol (13) and the (−)-acetate (14); these were simply separated by chromatography. The acetate was saponified to provide the antipode alcohol (−)-13. Rotations in dioxane (c=1) were +143° and −135° respectively. Oxidation of the alcohols with the catalytic system $CrO_3$-periodic acid provided the chiral acids (+)-15 and (−)-15 (rotations +208° and −197° resp in dioxane ). Ring closure of the acids in methanesulphonic acid provided the two enantiomers (+)-1 and (−)-1; dioxane(c=0,5)+129° resp −135°. The optically pure ketones can be converted, with full conservation of the absolute stereochemistry under the conditions described in scheme I, to the R- and S-enantiomers of the pharmacologically interesting antagonists Compounds described are potent and selective antagonists of the estrogen beta receptor relative to the alpha receptor. In the CHO transactivation assays (using an oxytocin promotor/luciferase readout system) selectivity ratios of up to a factor of 300 can be demonstrated. The relative stereochemistry of the three chiral centres in the compounds mentioned is very important, since the related cis,syn isomers (based upon positions of tertiary hydrogens, the isomer mentioned as found as minor side product in the reduction 4→5→6 )are considerably less active.

The compounds as such are interesting entities for modulation of the estrogen related malignant disturbances, and for use in estrogenic therapy required in relieve of typical discomforts associated with menopause. Their high selectivity of action makes them attracting pharmacological entities as adjuvant for improvement of hormonal treatments in which selective estrogen modulation is required. Apart from the uses described above the chemical stability is fairly high and therefore makes them attracting chemical entities to be used as drugs The present invention also relates to a pharmaceutical composition comprising the non-steroidal compound according to the invention mixed with a pharmaceutically acceptable auxiliary, such as described in the standard reference Gennaro et al, *Remmington: The Science and Practice of Pharmacy,* (20th ed., Lippincott Williams & Wilkins, 2000, see especially Part 5: Pharmaceutical Manufacturing). Suitable auxiliaries are made available in e.g. the Handbook of Pharmaceutical Excipients ($2^{nd}$ Edition, Editors A. Wade and P. J. Weller; American Pharmaceutical Association; Washington; The Pharmaceutical Press; London, 1994). The mixture of the compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the non-steroidal compound according to the invention for the manufacture of a medicament for estrogen-receptor related treatments and treatment of estrogen-receptor related disorders such as peri- and/or post-menopausal complaints. Thus the invention also pertains to the medical indications of peri- and/or post-menopausal (climacteric) complaints and osteoporosis, i.e. a method of treatment in the field of hormone replacement therapy (HRT), comprising the administration to a patient, being a woman, of a compound as described hereinbefore (in a suitable pharmaceutical dosage form).

Further, the invention relates to the use of the non-steroidal compound according to the invention in the manufacture of a medicament having contraceptive activity. Thus the invention also pertains to the medical indication of contraception, i.e. a method of contraception comprising the administration to a subject, being a woman or a female animal, of a progestogen and an estrogen as is customary in the field, wherein the estrogen is a compound as described hereinbefore (in a suitable pharmaceutical dosage form).

Finally the invention relates to the use of the non-steroidal compound for the manufacture of a medicament having selective estrogenic and/or anti-estrogenic activity, such a medicament being generally suitable in the area of HRT (hormone replacement therapy).

The estrogen-receptor affinity profile of the compounds according to the present invention, makes them suitable as improved anti-estrogens in the sense that they can be used for estrogen-receptor related medical treatments such as contraception or for treatment or prevention of benign prostate hypertrophy, cardiovascular disorders, menopausal complaints, osteoporosis, estrogen dependent tumour control or central nervous system disorders such as depression or Alzheimer's disease. Selective blockade of ERβ-receptors with compounds of this invention can be used to prevent and reduce malignant tumor growth and hyperplasias. The receptor selectivity helps to effectuate tissue selectivity. Those tissues rich in ERβ-receptors can be protected by ERβ-receptor antagonists from the risk of stimulation of growth by estrogenic agonists. The latter can be of endogenous origin or from exogenous origine when administered during estrogenic treatment, for example for hormone replacement after menopause. Tissues that can benefit from protection in view of the presence of ERβ-receptors are prostate, testes (human), lung, colon and endometrium. In particular, endometrium proliferation can be reduced by ERβ antagonists of the invention.

The dosage amounts of the present compounds will be of the normal order for estrogenic compounds, e.g. of the order of 0.01 to 100 mg per administration.

The invention is further illustrated hereinafter with reference to some unlimitative examples and the corresponding formula schemes referred to. Compounds are identified by numbers (in bold letter type) with reference to the corresponding numbers in the schemes. Abbreviations used in the schemes: Me is methyl, Bn is benzyl, ph is phenyl, aryl represents the substituted phenyl as in formula 1.

EXAMPLES

Compound 3

Grignard reagent was prepared from 500 mg of Mg (pre-activated by stirring in 3 ml of THF with 2 drops of 1,2-dibromoethane) and 4 ml (20 mmol) of m-bromophenol-O-trimethylsilylether in 38 ml of dry THF at 35° C. during 2 hr. The reagent was added dropwise to a solution of 275 mg of benzofluorenone 1 in a mixture of 3 ml of THF and 15 ml of ether at −20° C. After stirring for 2 hr the mixture was poured into 10% aqueous $NH_4Cl$ and extracted with ethyl acetate. The crude product (2) thus isolated was treated with 3 ml of 1M TBAF in THF and monitored by tlc. After stirring for 15 min the mixture was poured into 10% aq.$NH_4Cl$ and extracted with ethyl acetate. The crude product was purified by column chromatography (heptane/ethyl acetate as eluent) to provide 300 mg of 3 NMR (CDCl3) 7.30-6.60 (10H, Ar), 3.73, 3.78 (6, 2×OCH3) $R_f$ 0.20 (hept./ethyl ac. 6/4).

Compound 4

Before performing the dehydration of the tertiary alcohol, the phenol was protected as a tert.butyldimethylsilyl ether. 320 mg of 3 and 112 mg of imidazole in 2 ml of DMF were treated with 140 mg of tBDMSCl. After 2 hr the reaction was complete and the mixture was poured into water and the product extracted with ethyl acetate. Purification by passing through a short column gave 340 mg of silyl ether protected material. $R_f$ 0.59 (hept./eth. ac. 6/4).

This material was dissolved in 3 ml of dry pyridine and treated at −30° C. with 65 µl of $SOCl_2$. After stirring for 1 hr the mixture was poured into water and extracted with ethyl acetate. The product was purified by chromatography, to provide 220 mg of dihydrobenzoflourene 4;

NMR (CDCl3) 7.30-6.50 (10H, Ar), 4.05, (m, 1H), 3.88 (m, 1H), 3.47 (m, 1H), 3.21(m, 1H), 2.77(m, 1H), 3.68, 3.79 (6H, OCH3); $R_f$ 0.63 (hept./ethyl.ac 8/2).

Compound 5

A solution of 220 mg of 4 in a mixture of 12 ml of THF and 60 ml of liq. $NH_3$ was treated at −78° C. with small chips of Li until the blue color of the mixture persisted for 15 min. Then some solid $NH_4Cl$ was added until discharge of the color and the ammonia was allowed to evaporate. The residue was diluted with water and extracted with ethyl acetate, to give 180 mg of crude 5 The minor isomer present was removed after the next step; $R_f$ 0.65(hept./ethyl ac. 7/3),

Compound 6

180 mg of 5 was dissolved in 0.4 ml of 1M TBAF in THF and stirred for 15 min. The mixture was then poured into 10% $NH_4Cl$ solution and the product extracted into ethyl acetate. Purification was performed by passing through a silica column, to separate some unwanted isomer (using toluene/ethyl acetate as eluent). This gave 115 mg of the desired isomer 6 with ring junction cis and the aromatic side chain syn relative to these hydrogens (relative stereochemistry as indicated in the scheme). NMR (CDCl3) 2.70 (m, 2H), 3.07 (m, 2H) 3.22 (m, 1H), 3.54(m, 1H) 3.64 (m, 1H) 3.64(m, 1H)3.67, 3.78 (6H, OCH3), 6.28 (s, 1H, Ar) 6.67-7.30 (9, Ar H) $R_f$ 0.35 (hept./ethyl ac. 7/3). (minor isomer, all cis hydrogens, $R_f$ 0.38).

Compound 7

A mixture of 800 mg of 6 and 5 ml of 1,3-dibromopropane and 1.3 g of $K_2CO_3$ in 30 ml of acetonitrile was heated and stirred for 16 hr at 60° C. The mixture was then poured into water and extracted with ethyl acetate. The crude product was purified by chromatography and gave 960 mg of bromopropoxy ether 7;

NMR (CDCl3) 3.67, 3.78 (6, OCH3), 4.10 (t, 2H), 2.35 (m,2H) 2.65 (m, 2H), 3.08 (m, 2H) 3.23 (m, 1H) 3.60 (m, 4H); $R_f$ (hept./ethyl ac. 7/3) 0.66.

Compound 8

A mixture of 800 mg of 2 and 3 ml of 1,2-dibromoethane and 1.3 g of $K_2CO_3$ in 15 ml of acetonitrile was heated and stirred for 16 hr at 60° C. The mixture was then poured into water and extracted with ethyl acetate. The crude product was purified by chromatography and gave 960 mg of bromoethoxy ether 8; Mp 118-119° C.

NMR (CDCl3) 3.66, 3.77 (6, OCH3), 2.65 (m,2H), 3.08 (m, 2H), 3.22 (m, 1H), 3.52 (m, 1H), 3.64 (m, 3H) 4.30 (m, 2H), 6.25 (s, ArH), 6.65-7.36 (m, 9 ArH); $R_f$ (hept./ethyl ac. 7/3) 0.

Compound 9

A solution of 960 mg of 7 in 20 ml of methylene chloride was treated with 8 ml of $BF_3$.DMS. The reaction mixture was stirred for 16 hr and then poured into ice-water and extracted with ethyl acetate. The crude product was filtered through a short silica column (heptane/ethyl acetate as eluent) and gave 800 mg of 9; $R_f$ 0.29 (hept.ethyl ac 7/3). NMR (CDCl3) 2.30 (m, 2H), 2.67 (m, 2H), 3.05 (m, 2H), 3.20 (m, 1H), 3.51 (m, 1H)3.62 (m, 3H) 4.10(m, 2H) 6.61 (s, 1 ArH), 6.60-7.37 (9 ArH), 4.53 and 4.67 (2 s, OH)

Compound 10

A solution of 400 mg of 8 in 20 ml of methylene chloride was treated with 3.5 ml of $BF_3$.DMS. The reaction mixture was stirred for 16 hr and then poured into ice-water and extracted with ethyl acetate. The crude product was filtered through a short silica column (heptane/ethyl acetate as eluent) and gave 290 mg of 10; NMR (CDCl3) 2.63 (M, 2H), 3.06 (m, 2H), 3.20 (m, 1H), 3.80 (m, 1H) 3.68(m, 3H) 4.31 (m, 2H), 4.64 and 4.81 (2s, OH); $R_f$ 0.22 (hept./eth.ac 7/3).

Compound 11

A mixture consisting of 70 mg of bromide 9, and a secondary amine (generally 300 mg) in 2 ml of acetonitrile was heated at 50° C. during 16 hr at an oil bath. The reactions were poured into 10 ml of aqueous $NH_4Cl$ and the product extracted with ethyl acetate. Purification was done by passing through a short silcacolumn, using $CH_2Cl_2$/methanol as eluent. The products thus obtained were dissolved in ether and treated with an equivalent of an ethereal 1M solution of HCl. The HCl salts thus precipitated were dissolved in water, in the presence of some methanol or acetonitrile and freeze dried, to give the amines 11a-h. NMR spectra in DMSO confirmed the correct structures. LC-esi-MS was in accordance with the free bases of the structures assigned (11a, m 471; 11b, m 499; 11c, m 467; 11d, m 473; 11e, m 548; 11f, m 535; 11g, m 549; 11h, m 517)

Compound 12

A mixture consisting of 70 mg of bromide 10, and a secondary amine (generally 300 mg) in 2 ml of acetonitrile was heated at 50° C. during 16 hr at an oil bath. The reactions were poured into 10 ml of aqueous NH4Cl and the product extracted with ethyl acetate. Purification was done by passing through a short silcacolumn, using $CH_2Cl_2$/methanol as eluent. The products thus obtained were dissolved in ether and treated with an equivalent of an ethereal 1M solution of HCl. The HCl salts thus precipitated were dissolved in water, in the presence of some methanol or acetonitrile and freeze dried, to gave the amines 12a-c and 12i; NMR spectra in DMSO confirmed the correct structures. LC-esi-MS was in accordance with the free base of the structures assigned (12a, m 457; 12b, m 485; 12c, m 453; 12i, m 443)

SCHEME I
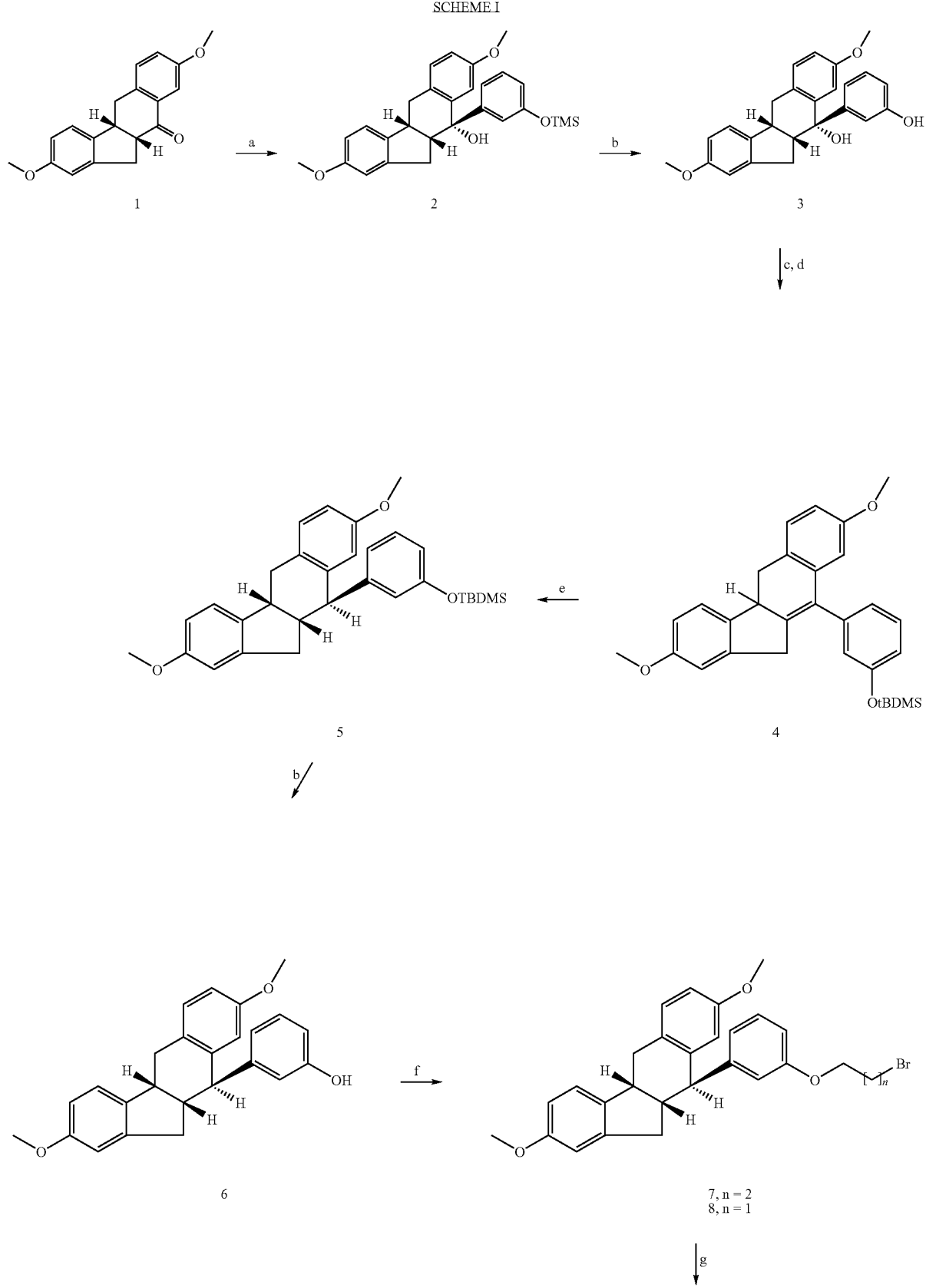

-continued
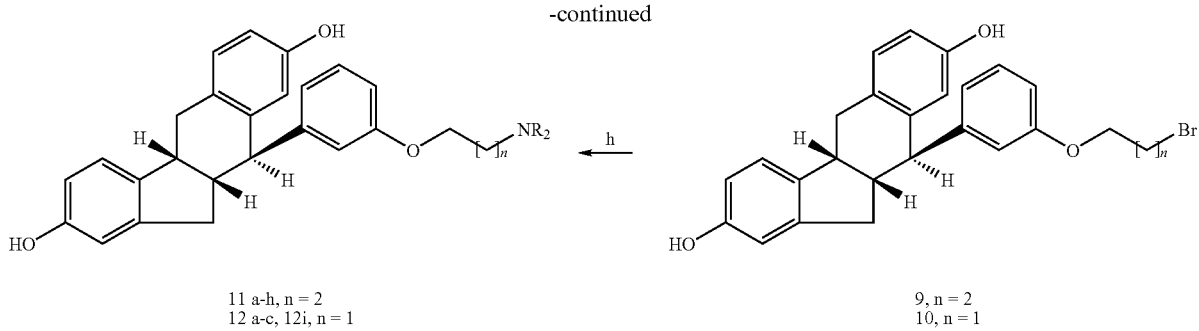
11 a–h, n = 2
12 a–c, 12i, n = 1
9, n = 2
10, n = 1
a) 1-bromo-3-(trimethylsiloxy)benzene, Mg in THF
b) 1M TBAF in THF
c) TBDMS-Cl, imidazole in DMF
d) SOCl2/pyridine, −30° C.
e) Li, NH3, −78° C.
f) 1,2-dibromoethane or 1,3-dibromopropane, K2CO3, acetonitrile, 60° C.
g) BF3·DMS in CH2Cl2
h) HNR2 in acetonitrile
amines used a–i
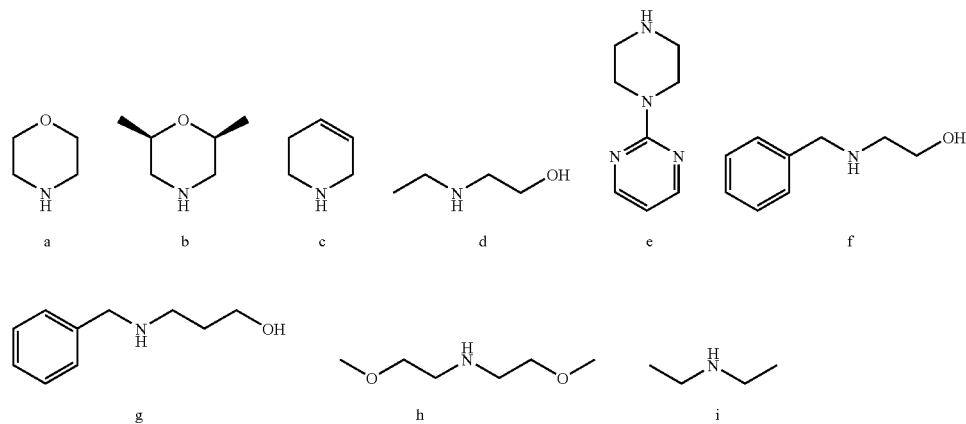
Formula II
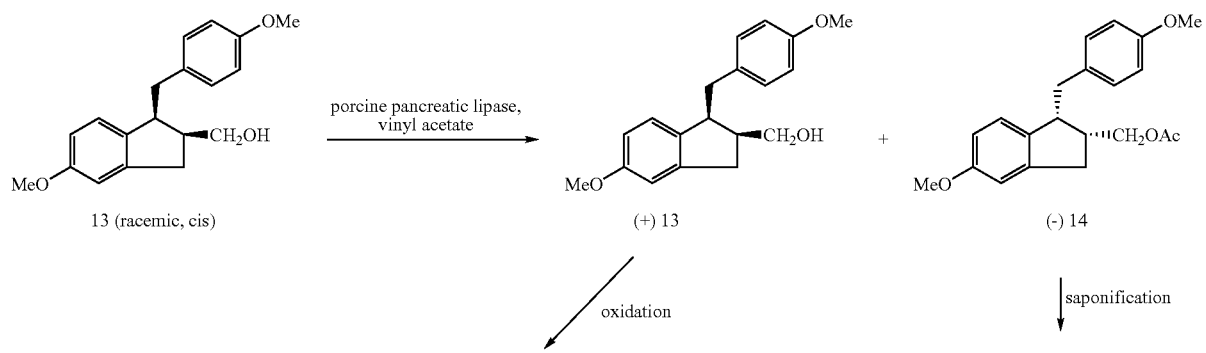

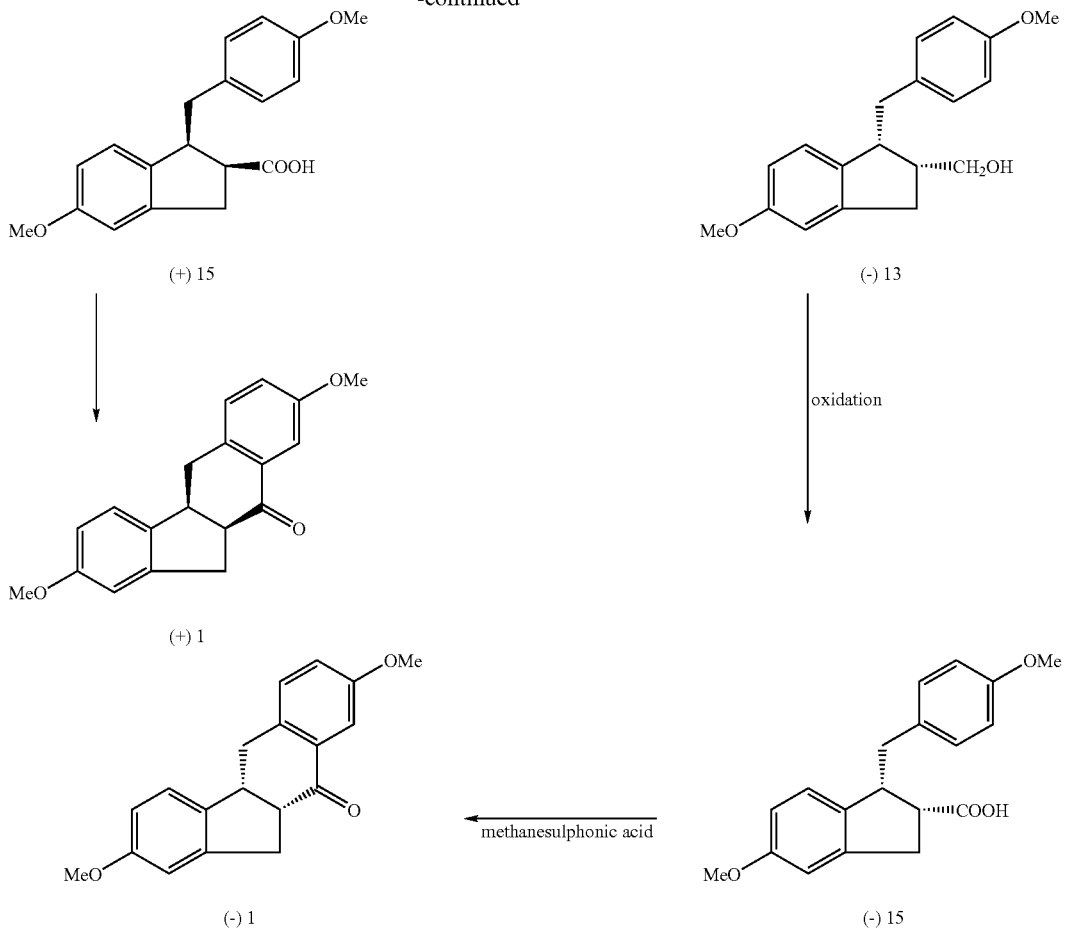

I claim:

1. A method of treating osteoporosis, the method comprising administering to a patient an effective amount of the compound having the formula I

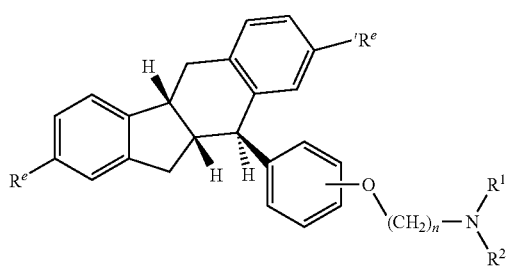

Formula I wherein
the O—(CH$_2$)$_n$—N(R$^1$,R$^2$) substituent on the phenyl ring can be in meta or para position;
n is 2-4
R$^e$ and 'R$^e$ are OH, optionally independently etherified or esterified;
R$^1$ and R$^2$ are independently (1C-4C)alkyl, (2C-4C)alkenyl, hydroxy(2C-4C)alkyl, (1C-3C)alkoxy(2C-4C)alkyl, aryl or aryl(1C-2C)alkyl; or R$^1$ and R$^2$ together with the nitrogen form an aromatic or non-aromatic heterocyclic ring structure, optionally mono- or polysubstituted with (1C-4C)alkyl, (2C-4C)alkenyl, hydroxy(1C-2C)alkyl, (1C-2C)alkoxy(1C-3C)alkyl or aryl.

2. The method according to claim 1, wherein in the compound having the formula I, the O—(CH$_2$)$_n$—N(R$^1$,R$^2$) substituent on the phenyl ring is in the meta position;
n is 2 or 3;
R$^e$ and 'R$^e$ are OH; and
R$^1$ and R$^2$ independently are benzyl, (1C-4C)alkyl, hydroxy(2C-4C)alkyl, (1C-3C)alkoxy(2C-4C)alkyl or together with the nitrogen form a non-aromatic ring selected from the list morpholino, piperidino, pyrrolidino, tetrahydropyridyl and piperazinyl, wherein the morpholino, piperidino, pyrrolidino, tetrahydropyridyl can be optionally substituted with (1C-2C)alkyl and the piperazinyl can be optionally substituted at distal nitrogen (4) with (1C-4C)alkyl, (2C-4C)alkenyl, (1C-2C) alkoxy(1C-2C)alkyl or aryl.

3. A method of contraception, the method comprising administering to a patient an effective amount of a compound having the formula I

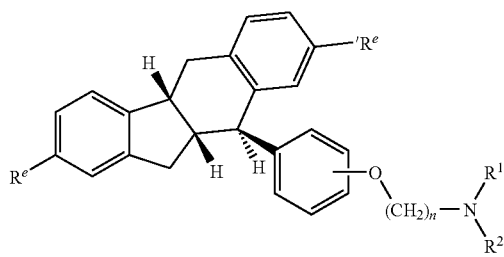

Formula I wherein
the O—(CH$_2$)$_n$—N(R$^1$,R$^2$) substituent on the phenyl ring can be in meta or para position;
n is 2-4
R$^e$ and 'R$^e$ are OH, optionally independently etherified or esterified;
R$^1$ and R$^2$ are independently (1C-4C)alkyl, (2C-4C)alkenyl, hydroxy(2C-4C)alkyl, (1C-3C)alkoxy(2C-4C)alkyl, aryl or aryl(1C-2C)alkyl; or R$^1$ and R$^2$ together with the nitrogen form an aromatic or non-aromatic heterocyclic ring structure, optionally mono- or poly-substituted with (1C-4C)alkyl, (2C-4C)alkenyl, hydroxy(1C-2C)alkyl, (1C-2C)alkoxy(1C-3C)alkyl or aryl.

4. The method according to claim 3, whereby the O—(CH$_2$)$_n$—N(R$^1$,R$^2$) substituent on the phenyl ring is in the meta position;
n is 2 or 3;
R$^e$ and 'R$^e$ are OH; and
R$^1$ and R$^2$ independently are benzyl, (1C-4C)alkyl, hydroxy(2C-4C)alkyl, (1C-3C)alkoxy(2C-4C)alkyl or together with the nitrogen form a non-aromatic ring selected from the list morpholino, piperidino, pyrrolidino, tetrahydropyridyl and piperazinyl, whereby the morpholino, piperidino, pyrrolidino, tetrahydropyridyl can be optionally substituted with (1C-2C)alkyl and the piperazinyl can be optionally substituted at distal nitrogen (4) with (1C-4C)alkyl, (2C-4C)alkenyl, (1C-2C)alkoxy(1C-2C)alkyl or aryl.

5. The method according to claim 2, wherein
n=3; and
R$^1$ and R$^2$ independently are benzyl or hydroxypropyl.

* * * * *